United States Patent
Schmidt

(10) Patent No.: US 9,422,327 B2
(45) Date of Patent: Aug. 23, 2016

(54) PROCESS FOR PREPARING CRYSTALLINE CICLESONIDE WITH DEFINED PARTICLE SIZE

(75) Inventor: Beate Schmidt, Allensbach (DE)

(73) Assignee: TAKEDA GMBH, Constance (DE)

( * ) Notice: Subject to any disclaimer, the term of this patent is extended or adjusted under 35 U.S.C. 154(b) by 3074 days.

(21) Appl. No.: 10/549,631

(22) PCT Filed: Mar. 26, 2004

(86) PCT No.: PCT/EP2004/050373
§ 371 (c)(1),
(2), (4) Date: Nov. 7, 2005

(87) PCT Pub. No.: WO2004/085460
PCT Pub. Date: Oct. 7, 2004

(65) Prior Publication Data
US 2006/0128954 A1    Jun. 15, 2006

(30) Foreign Application Priority Data

Mar. 27, 2003 (DE) .................................. 103 14 097
Mar. 27, 2003 (EP) .................................... 03007007

(51) Int. Cl.
*C07J 71/00* (2006.01)

(52) U.S. Cl.
CPC ...................................... *C07J 71/00* (2013.01)

(58) Field of Classification Search
CPC ...................................................... C07J 71/00
See application file for complete search history.

(56) References Cited

U.S. PATENT DOCUMENTS

| | | | |
|---|---|---|---|
| 4,605,517 A | 8/1986 | Riley et al. | |
| 5,482,934 A | 1/1996 | Calatayud et al. | |
| 5,728,826 A | 3/1998 | Gutterer | |
| 5,733,901 A | 3/1998 | Gutterer | |
| 6,120,752 A | 9/2000 | Oliver et al. | |
| 6,264,923 B1 | 7/2001 | Oliver et al. | |
| 6,482,438 B1 | 11/2002 | Singh et al. | |
| 6,585,958 B1 * | 7/2003 | Keller et al. | 424/45 |
| 6,787,533 B1 | 9/2004 | Gutterer | |
| 2005/0080063 A1 | 4/2005 | Schmidt | |

FOREIGN PATENT DOCUMENTS

| | | | |
|---|---|---|---|
| DE | 41 29 535 A1 | 3/1992 | |
| DE | 195 41 689 A1 | 5/1996 | |
| DE | 196 35 498 A1 | 3/1998 | |
| DE | WO98/09982 * | 3/1998 | ............... C07J 71/00 |
| EP | 0 142 309 A2 | 5/1985 | |
| EP | 0 142 309 B1 | 5/1985 | |
| EP | 0 407 028 B1 | 1/1991 | |
| EP | 0 505 321 A2 | 9/1992 | |
| EP | 0 650 410 B1 | 5/1995 | |
| EP | 0 691 865 B1 | 1/1996 | |
| EP | 0 725 725 B1 | 8/1996 | |
| WO | 90/03782 A2 | 4/1990 | |
| WO | 92/08730 A1 | 5/1992 | |
| WO | 98/09982 A1 | 3/1998 | |
| WO | 99/21601 A1 | 5/1999 | |
| WO | 00/38811 A1 | 7/2000 | |
| WO | 01/00046 A1 | 1/2001 | |
| WO | 01/28562 A1 | 4/2001 | |
| WO | 01/28563 A1 | 4/2001 | |
| WO | 02/38584 A1 | 5/2002 | |

OTHER PUBLICATIONS

Merck Manual (1996).*
Sudha Vippagunta, Harry Brittain & David Grant, Crystalline Solids, 48 Adv. Drug Del. Rev. 3 (2001).*
Ruch, F, Matijevic, E., "Preparation of Micrometer Size Budesonide Particles by Precipitation", *Journal of Colloid and Interface Science*, vol. 229, pp. 207-211.
Hem, S.L. et al., "Mechanism of Crystallization of Hydrocortisone by Ultrasonic Irradiation", *J. of Pharm. Sciences*, vol. 56, No. 2, pp. 229-233 (1967).
Sjostrom, B. et al., "A Method for the Preparation of Submicron Particles of Sparingly Water-Soluble Drugs by Precipitation in Oil-in-Water Emulsions. II: Influence of the Emulsifier, the Solvent, and the Drug Substance", *J. of Pharm. Sciences*, vol. 82, No. 6, pp. 584-589 (1993).

* cited by examiner

*Primary Examiner* — Sean Basquill
(74) *Attorney, Agent, or Firm* — Nath, Goldberg & Meyer; Joshua B. Goldberg; Scott H. Blackman

(57) ABSTRACT

The invention relates to a novel process for preparing crystalline ciclesonide with an advantageous particle size and to the use for producing pharmaceutical preparations, in particular for topical use. The crystalline ciclesonide obtained by the novel process has advantageous aerodynamic properties, and can be further processed to inhalable or nasally administered pharmaceutical preparations without further mechanical micronization.

16 Claims, No Drawings

PROCESS FOR PREPARING CRYSTALLINE CICLESONIDE WITH DEFINED PARTICLE SIZE

FIELD OF THE INVENTION

The invention relates to a novel process for preparing crystalline ciclesonide with an advantageous particle size and particle size distribution and to the use for producing pharmaceutical preparations, in particular for topical use. The crystalline ciclesonide obtained by the novel process has advantageous properties, in particular for further processing to inhalable or nasally administered pharmaceutical preparations.

KNOWN TECHNICAL BACKGROUND

U.S. Pat. No. 4,605,517 is related to a method of preparing steroid compounds of controlled particle size comprising dissolving the steroid in an organic solvent, precipitating the steroid by mixing a non-solvent for the steroid with the resulting solution, and controlling the time of mixing and the degree of agitation during mixing.

Sjoestroem et al. [J. Pharm. Sci (1993) 82(6), 584-9] describe a process for preparing small particles of sparingly water-soluble active compounds by precipitation in oil-water emulsions. For this purpose, the steroids cholesteryl acetate and β-sitosterol were dissolved in an organic solvent, and an emulsion was prepared with water in the presence of a surfactant. Evaporation of the organic solvent results in a precipitate of the steroid with particle sizes down to 25 nm.

Hem et al. [J. Pharm. Sci (1967), 56(2), 229-233] describe the mechanism of crystallization of hydrocortisone on exposure to ultrasound.

EP 142309 A2 describes the preparation of active compounds by dissolving in an organic solvent and mixing with a non-solvent for the active compound. Epostane was for this purpose dissolved in dimethylformamide (DMF), and water was added. The precipitate obtained in this way has particle sizes which are within a narrow size range.

Ruch et al. [Journal of Colloid and interface Science (2000), 229(1), 207-211] describe the preparation of budesonide particles in the micrometer size range by precipitation in an ultrasonic bath. For this purpose, water is added to budesonide solutions exposed to ultrasound until a precipitate is obtained or, in the case where budesonide is dissolved in solvent mixtures, the more volatile solvent is evaporated at room temperature.

WO 90/03782 relates to a process for preparing a finely divided solid by dissolving the solid in a liquid carrier solvent in order to form an injection solution, and adding the injection solution to an antisolvent which is a supercritical fluid, a compressed, liquefied gas or a dense vapour.

WO 92/08730 describes a process for crystallizing organic substances, especially steroids. For this purpose, the steroid is dissolved in a ternary mixture of lipophilic solvent, hydrophilic solvent and a surface-active substance, and crystallized. This is said to result in predeterminable and homogeneous particle sizes by non-mechanical means.

Ciclesonide is the INN (International Nonproprietary Name) for a compound with the chemical name 16,17-[(cyclohexylmethylene)bis(oxy)]-11-hydroxy-21-(2-methyl-1-oxopropoxy)pregna-1,4-diene-3,20-dione [11 beta, 16alpha (R)]. The preparation of ciclesonide and other epimeric pregna-1,4-diene-3,20-dione 16,17-acetal 21-esters with anti-inflammatory effect having a butyl, isopropyl, sec-butyl, cyclohexyl or phenyl radical on the cyclic acetal ring, and whose C-21 hydroxyl group is acylated by an acetyl or isobutyryl radical, are disclosed in DE-A 41 29 535. Isolation of the respective R epimer starting from an R/S mixture by preparative high-pressure liquid chromatography (HPLC) is described. The international patent application WO 98/09982 A1 describes a process for epimer enrichment of the R epimer of ciclesonide by fractional crystallization. For this purpose, ciclesonide in the form of an R/S mixture is dissolved in a suitable water-miscible organic solvent at the boiling point, water is added, and the mixture is cooled to room temperature. The R epimer-enriched ciclesonide obtained in this way must, however, then be subjected to a mechanical micro on in order to obtain the particle sizes and distributions necessary for inhalable pharmaceutical preparations. It would be desirable during the chemical synthesis of ciclesonide to obtain the active compound as product of the process already in form having particle sizes and distribution suitable immediately for further processing to inhalable preparations. This would make it possible to dispense with the additional mechanical micronization and thus possible disadvantages of a mechanical micronization [e.g. risk of contamination, formation of particles which are too small, increased uptake of water owing to the amorphous structures of the micronized product compared with crystalline structures] could be avoided.

DESCRIPTION OF THE INVENTION

It has now been found, surprisingly, that dissolution of ciclesonide in a water-miscible solvent and subsequent addition of this ciclesonide solution to water results in crystalline ciclesonide which—in contrast to the ciclesonide obtained by the process described in WO 98/09982 A1—has particle sizes which are suitable for inhalation. It is therefore possible in the further processing to inhalable pharmaceutical preparations to dispense with mechanical micronization.

The invention therefore relates to a process for preparing a compound of the formula I

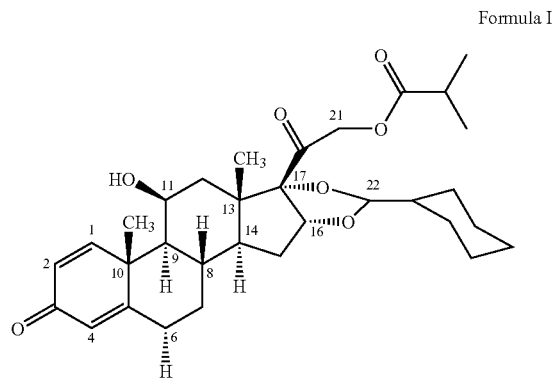

Formula I

In crystalline form, with defined particle size, comprising the steps of
  a) preparation of a solution of the compound of the formula I in a suitable water-miscible organic solvent;
  b) adding the solution obtained as in a) to water and
  c) isolating the precipitate of the compound of the formula I which is formed.

The compound of the formula I is a compound with the chemical name 16,17-[(cyclohexylmethylene)bis(oxy)]-11-hydroxy-21-(2-methyl)-1-oxopropoxy)pregna-1,4-diene-3, 20-dione [11 beta, 16alpha (R,S)]. The R epimer (based on the absolute configuration at C-22) of this compound has the INN (International Nonproprietary Name) ciclesonide. The term compound of the formula I encompasses according to the invention the pure R epimer, the pure S epimer, and R/S epimer mixtures in any mixing ratio and also pharmaceutically acceptable solvates of the compound of the formula I.

The procedure for the process of the invention advantageously starts from a compound of the formula I which is mainly in the form of the R epimer (based on the absolute configuration at C-22). Mainly in epimerically pure form means in this connection according to the invention that at least 90%, preferably at least 95%, in particular at least 97%, particularly preferably at least 99%, of the R epimer is present. Such compounds of the formula I which are mainly in the form of the R epimer can be obtained for example in analogy to the synthesis process described in WO 02/38584 and subsequent acylation or by preparative HPLC or fractional crystallization of R/S epimer mixtures of the compound of the formula I as described in the international patent application WO 98/09982.

To carry out the process of the invention, the compound of the formula I is dissolved in a suitable water-miscible organic solvent. Suitable water-miscible organic solvents which may be mentioned according to the invention are alcohols such as, for example, methanol, ethanol, N-propanol and isopropanol, acetone, tetrahydrofuran (THF) or dimethylformamide (DMF) and mixtures thereof in any mixing ratio. It is expedient for the solvent to have a temperature during this of from 10° C. to the boiling point of the solvent, preferably a temperature of from 15° C. to a temperature which is 10° C. below the boiling point of the solvent, in particular from 15° C. to 35° C., particularly preferably from 20° C. to 25° C., and the solvent is very particularly preferably at room temperature (i.e. temperature of the solvent corresponds to the temperature of the room where the process is carried out). The subsequent addition of this solution to water expediently takes place with stirring and while maintaining the temperature of the solvent. The addition particularly preferably takes place by dropwise addition. The temperature of the water is according to the invention preferably from 10° to 50° C., preferably 15° C. to 40° C., very particularly preferably 20° C. to 30° C. In a preferred embodiment, the water is at room temperature (i.e. temperature of the water corresponds to the temperature of the room where the process is carried out). The amount of the solvent used to dissolve the compound of the formula I depends on the nature of the solvent and the temperature. It is expedient to use at least sufficient solvent for the compound of the formula I to be completely dissolved, preferably somewhat more. The amount of water employed in the process of the invention is expediently to be chosen so that the dissolved compound of the formula I is precipitated in quantitative form after addition to the water.

The precipitate which is formed is isolated according to the invention preferably by removing the precipitate from the solution, in particular by filtering off the precipitate, washing the precipitate with water and subsequently drying.

The process of the invention results in the compound of the formula I with a defined particle size. The defined particle size is according to the invention a partake size and particle distribution suitable for inhalation. A form suitable for inhalation means particle sizes having an aerodynamic diameter between 1 and 10 µm, preferably in the range from 1 to 5 µm, particularly preferably 1 to 3 µm. Preparations which are preferred in this connection are those for which the particle size determination shows an $X_{60}$[unit: µm] of less than or equal to 10, preferably 7.5, very preferably 3, particularly preferably 2. An $X_{60}$ in the range from 1.8 to 2.0 is to be particularly emphasized according to the invention. The $X_{60}$ in the particle size determination means that the particle diameter for 50% of the total volume of all the particles is less than the stated value. Determination of the particle size distribution is possible, for example, by laser diffraction on the solid substance by known methods. It is preferred according to the invention for the particle size distribution to be determined according to by the dry measurement method like that used for example in the Sympatec HELOS-LASER diffractor or an equivalent instrument (the instrument parameters on the Sympatec HELOS-LASER diffractor can be set as follows, for example: measurement time (5 s), time base (1 000 ms), reference measurement duration (5 s), measurement range/lens (R2 0.25/0.45 0.87.5 µm), starting condition(0.000 s after starting button), dispersing module (RHODOS+VIBRI), evaluation mode (HRLD), bed height (2 mm), output (50%), dispersing pressure (3.50 bar, permitted variation in the actually measured pressure is 3.30 bar to 3.70 bar and evaluation of the Fraunhofer diffraction diagram).

Preference is given according to the invention to a crystalline inhalable form of the compound of the formula I having a maximum proportion of particles with the particle size in the range from 1.5 µm to 7.5 µm, preferably 1.75 µm to 6.5 µm, particularly preferably 1.85 µm to 5.5 µm, in particular 2 µm to 5 µm. This range represents the inhalable fraction which, because of its size, is not deposited directly in the mouth or throat on inhalation or is exhaled again because of its fineness). An exemplary embodiment of the invention is a crystalline inhalable form of the compound of the formula I in which a maximum of 55% (vol.) of the particles are smaller than or equal to 1.85 µm, and at least 75% [vol.] are smaller than or equal to 45 µm. The compound preferably is not in micronised form. Micronised form according to the invention means that the compound has been subject to a mechanical microrization step (e.g. mechanical milling).

The compound of the formula I can be prepared in a manner known per se, for example as described in DE-A 41 29 535. Alternatively, the compounds of the formula I can also be prepared starting from the corresponding 21-hydroxy compounds of the formula II

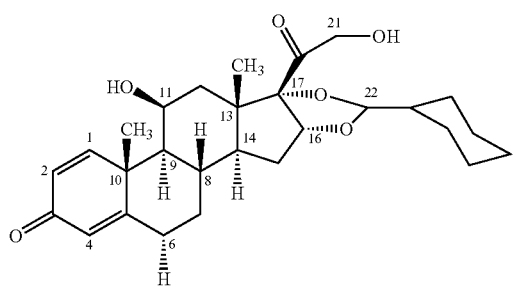

Formula II by acylation with a suitable acylating agent. Such 21-hydroxy compounds are described for example in WO 95/24416 and WO 02/38584. The acylation can in this case take place in a manner known to the skilled person, e.g. as described in WO 98/09982.

The invention therefore further also relates to a process for preparing a compound of the formula I

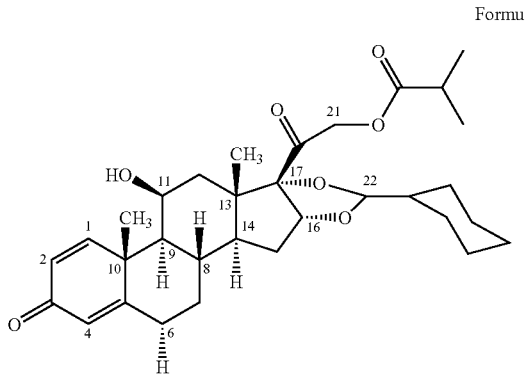

Formula I in crystalline form with defined particle size, comprising the steps of
a) preparing a compound of the formula I by acylation of a compound of the formula II with a suitable acylating agent;
b) crystallizing the compound of the formula I obtained in a) by adding water to a solution of the compound in a suitable water-miscible organic solvent or heating a suspension of the compound of the formula I in a mixture of a suitable water-miscible organic solvent and water,
c) removing the resulting R epimer-enriched precipitate of the compound of the formula I from the water/solvent mixture;
d) if desired repeating step b);
e) preparing a solution of the compound obtained in c) in a suitable water-miscible organic solvent;
f) adding the solution obtained as in e) to water and
g) isolating the precipitate which has been formed of the compound of the formula I.

To carry out steps a), b) and c) of the process of the invention, the R/S epimer mixture of the formula I is dissolved in a suitable water-miscible organic solvent, expediently at elevated temperature, in particular at the boiling point of the solvent used. The subsequent addition of water to this solution expediently takes place with stirring and while maintaining the elevated temperature, in particular the boiling point, with a cooling, preferably to room temperature, taking place with stirring after the addition of water is complete. Alternatively, the R/S epimer mixture of the formula I can be suspended in a mixture of water and a suitable water-miscible organic solvent and be dissolved by heating, in particular to the boiling point of the solvent mixture. The solution is subsequently cooled while stirring, preferably to room temperature. The cooling advantageously takes place slowly, preferably over a period of from 2 to 10 hours. The subsequent fractional crystallization can advantageously be influenced by adding crystallization nuclei (e.g. seed crystals), preferably using seed crystals of the pure R epimer of the formula I in each case. Examples of suitable water-miscible organic solvents which may be mentioned for step b) of the process of the invention are acetone or, in particular, alcohols such as isopropanol, n-propanol, methanol and, preferably, ethanol, and mixtures thereof in any mixing ratio. It is expedient to use for dissolving 0.18 mol of R/S epimer mixture of the formula 190-700 ml of the suitable water-miscible organic solvent, preferably 300-400 ml. The ratio of the water to the water-miscible organic solvent by volume is preferably in the range between 0.1-1 [v/v], in particular between 0.25-0.75[v/v].

The subsequent removal [step c)] of the R epimer-enriched R/S epimer mixture of the formula I from the solution takes place in a manner known to the skilled person, in particular by filtration.

The procedure for the process of the invention advantageously starts from compounds of the formula I in which the R epimer is already enriched, for example the R epimer content is ≥75%, in particular ≥85%. The acylation in step a) moreover takes place in a manner known to the skilled person, e.g. as described in the examples by acylation with suitable acylating agents such as isobutyric anhydride.

The crystalline compound of the formula I with defined particle size obtained by the process of the invention can then be further processed to pharmaceutical preparations (preferably without further micronization step), where appropriate in combination with further pharmaceutical active compounds. The compound of the formula I are employed in the pharmaceutical preparations either as such or, preferably, in combination with suitable pharmaceutical excipients, e.g. in the form of tablets, coated tablets, capsules, suppositories, plasters, emulsions, suspensions, gels or solutions, with the active compound content advantageously being between 0.1 and 95%. Pharmaceutical preparations which are preferably mentioned are those for topical administration through the lungs and through mucous membranes, especially the nasal mucosa.

The excipients suitable for the desired pharmaceutical preparation are familiar to the skilled person on the basis of his expert knowledge. Besides solvents, gal formers, ointment bases and other active compound carriers, it is possible to use for example antioxidants, dispersants, emulsifiers, preservatives, solubilizers or permeation promoters.

The compound of the formula I obtained by the process of the invention is administered for the treatment of disorders of the respiratory tract preferably in inhaled form. For this purpose, the compound of the formula I is administered either directly as powder or atomization of solutions or suspensions containing it. The substances are for this purpose preferably administered by inhalation in the form of aerosols, with the aerosol particles of solid, liquid or mixed composition having a diameter of from 0.5 to 10 µm, advantageously from 2 to 6 µm.

The aerosol can be generated for example by pressure-operated nozzle nebulizers or ultrasonic nebulizers, but advantageously by propellant gas-operated metered aerosols or propellant gas-free use of micronized active compounds from inhalation capsules.

Depending on the inhaler system used, the pharmaceutical preparations comprise besides the active compounds also the necessary excipients such as, for example, propellant gases (e.g. HFA 134a or 227), solvents (e.g. ethanol, surface-active substances, emulsifiers, stabilizers, preservatives, aromatizing agents, fillers (e.g. lactose for powder inhalers) or, where appropriate, further active compounds.

Pharmaceutical preparations of ciclesonide suitable for inhalation or for administration to nasal mucosa, and the production, are described for example in U.S. Pat. No. 6,120,752, U.S. Pat. No. 5,264,923, WO01/028562, WO01/028563 or DE 19541689. The pharmaceutical preparations can be produced by processes known to the skilled person. Normally, the active compounds (i.e. the compound of the formula I, if desired combined with further active compounds) are mixed with a carrier, which consists of one or more excipients. In this case, the active compounds are generally finely divided in solid and/or liquid carriers and then further processed to the desired pharmaceutical preparation.

For inhalation purposes there are available a large number of appliances with which aerosols of optimal particle size can be generated and administered using an inhalation technique which is as appropriate as possible for the patent. Besides the use of attachments (spacers, expanders) and pear-shaped containers (e.g. Nebulator®, Volumatic®) and automatic delivery actuations (Autohalar®) for metered aerosols, a series of technical solutions are available in particular for powder inhales (e.g. Diskhalar®, Rotadisk®, Turbohaler® or the technologies described in EP 0 505 321, EP 407028, EP 650410, EP 691865, EP 725725, WO99/21601, U.S. Pat. No. 6,120,752 or U.S. Pat. No. 6,264,923), with which optimal administration of active compound can be achieved.

Concerning the composition and production of pharmaceutical preparations for nasal administration, reference is made for example to WO 01/28562 and WO 01/28563.

The following examples illustrate the invention further without restricting it. RT stands for room temperature, min for minute(s), h for hour(s), m.p. for melting point and abs. for absolute.

EXAMPLES

1. Preparation of crystalline 16,17-[(cyclohexylmethylene)bis(oxy)]-11-hydroxy-21-methyl-1-oxopropoxy)pregna-1,4-diene-3,20-dione [11beta, 16alpha(R,S)] with defined particle size 16,17-[(Cyclohexylmethylene)bis(oxy)]-11-hydroxy-21-(2-methyl-1-oxopropoxy)pregna-1,4-diene-3,20 dione [11beta, 16alpha (R,S)] is dissolved at the temperature indicated in the table in the appropriate amount of ethanol. The solution is added dropwise, while maintaining the temperature and with vigorous stirring, to the stated amount of water at the stated temperature of the water. The precipitate is filtered off with suction, washed with water and dried.

The $X_{50}$ in the table is determined by laser diffraction by the dry measurement method in a Sympatec HELOS-LASER diffractor or an equivalent instrument [parameters: measurement time (5 s), time base (1 000 ms), reference measurement duration (5 s), measurement range/lens (R20.25/0.45 0.87.5 μm), starting condition (0.000 s after starting button), dispersing module (RHODOS+VIBRI), evaluation mode (HRLD), bad height (2 mm), output (50%), dispersing pressure (3.50 bar, permitted variation of the actually measured pressure is 3.30 bar to 3.70 bar and evaluation of the Fraunhofer diffraction diagram)]. In contrast to the crystallization process described in WO 98/09982, no epimer enrichment is observed.

| Example | Ethanol (ml/g) | Ethanol temp. (° C.). | Water (ml/g) | Water temp. (° C.) | Yield (%) | $X_{50}$ (μm) |
|---|---|---|---|---|---|---|
| 1 | 5 | RT | 25.5 | RT | 94 | 2.0 |
| 2 | 7.5 | RT | 25.5 | RT | 95 | 1.8 |
| 3 | 7.5 | RT | 12.5 | RT | 95-98 | 1.9 |
| 4 | 7.5 | RT | 7.5 | RT | 96 | 2.0 |
| 5 | 7.5 | RT | 12.5 | 10 | 94-96 | 1.6 |
| 6 | 7.5 | RT | 12.5 | 30 | 92-95 | 1.9 |
| 7 | 7 | RT | 10 | RT | 97 | 1.8 |
| 8 | 7 | RT | 12 | 40 | 97 | 1.8 |
| 9 | 6 | RT | 10 | 20 | 90-97 | 1.8 |

-continued

| Example | Ethanol (ml/g) | Ethanol temp. (° C.). | Water (ml/g) | Water temp. (° C.) | Yield (%) | $X_{50}$ (μm) |
|---|---|---|---|---|---|---|
| 10 | 6 | RT | 6 | 20 | 97 | 2.0 |
| 11 | 2.2 | 50 | 6 | 20 | 96-98 | 1.8 |
| 12 | 2.2 | 50 | 10 | 20 | 96 | 2.8 |
| 13 | 3 | 40 | 7 | 20 | 96 | 2.1 |
| 14 | 4 | 30 | 8 | 20 | 96 | 1.8 |
| 15 | 4 | 30 | 8 | 30 | 96-97 | 1.9 |
| 16 | 10 | 20 | 10 | 20 | 97 | 1.9 |

2. Epimer enrichment of 16,17-[(cyclohexylmethylene)bis(oxy)]-11-hydroxy-21-(2-methyl-1-oxopropoxy)pregna-1,4-diene-3,20-dione[11beta, 16alpha(R,S)] by the process described in WO 98/09982

2.1 316 g (584 mmol) of 16,17-[(cyclohexylmethylene)bis(oxy)]11-hydroxy-21-(2-methyl-1-oxopropoxy)pregna-1,4-diene-3,20-dione [11beta, 16alpha (R,S)], referred to as A hereinafter, (crude product, oil, R/S epimer ratio about 90/10) are dissolved in 1.1 l of abs, ethanol and, while boiling, 700 ml of water are added. The mixture is allowed to reach RT while stirring vigorously, and the precipitate is filtered off with suction, washed with 500 ml of abs. ethanol/water 2/1 and dried in a vacuum oven at 50° C. for 5 h.

Yield: 237 g (438 mmol, 75%) of A, R/S epimer ratio about 95/5.

m.p.: 199-201° C.

The product is dissolved in 900 ml of abs, ethanol and, while boiling, 650 ml of water are added, and the product is isolated as stated above.

Yield: 209 g (386.5 mmol, 88%) of A, R/S epimer ratio about 97/3.

m.p.: 201-203° C.

The product is dissolved in 800 ml of abs, ethanol and, while boiling, 450 ml of water are added, and the product is isolated as stated above.

Yield: 178 g (329 mmol, 85%) of A, R/S epimer ratio about 98.5/1.5.

m.p.: 205-206° C.

The product is dissolved in 600 ml of abs. ethanol and, while boiling, 350 ml of water are added, and the product is isolated as stated above.

Yield: 161 g (298 mmol 90.5%) of A, R/S epimer ratio>99.5/0.5.

m.p.: 206.5-207° C.

2.2 1.5 g (2.77 mmol) of A (R/S epimer ratio about 89/11) are dissolved in 3 ml of abs. methanol and, while boiling, 1 ml of water is added. The mixture is allowed to reach RT while stirring, and the precipitate is filtered off with suction, washed with a little methanol/water=3/1 and dried as above.

Yield: 1.21 g (80.6%) of A, R/S epimer ratio about 93:7.

2.3 5 g (9.25 mmol) of A (R/S epimer ratio about 91.5/8.5) are dissolved in 15 ml of boiling isopropanol, and 10 ml of water are added. The mixture is allowed to reach RT while stirring, and the precipitate is filtered off with suction, washed with a little isopropanol/water 2/1 and dried as above.

Yield: 4 g (80%) of A, R/S epimer ratio about 94/6.

2.4 1.5 g (2.77 mmol) of A (R/S epimer ratio about 89/11) are dissolved in 4 ml of boiling acetone, and 1 ml of water is added. The mixture is allowed to reach RT while stirring, and the precipitate is filtered off with suction, washed with a little acetone/water=2/1 and dried as above.

Yield: 1.12 g (75%) of A, R/S epimer ratio about 95/5.

3. $X_{60}$ vales for 16,17-[(cyclohexylmethylene)bis (oxy)]-11-hydroxy-21-[2-methyl-1-oxopropoxy) pregna-1,4-diene-3,20-dione[11beta, 16alpha (R,S)] obtained by fractional crystallization by the process described in WO 83/09982

The following table contains $X_{60}$ values for 16,17-[(cyclohexylmethylene)bis(oxy)]-11-hydroxy-21-(2-methyl-1-oxopropoxy)pregna-1,4-diene-3,20-dione [11beta, 16alpha (R,S)] obtained by the process described in WO 98/09982 (see Example 2). The $X_6$ is determined by a suitable process. The ethanol/water column relates to the ratio of ethanol to water by volume used for the crystallization.

| Example | Ethanol/water | $X_{50}$ (μm) |
|---|---|---|
| 1 | 1/0.65 | 26.57 |
| 2 | 1/0.55 | 33.79 |
| 3 | 1/0.6 | 35.25 |
| 4 | 1/0.7 | 21.82 |
| 5 | 1/0.4 | 37.02 |
| 6 | 1/0.8 | 20.83 |

Result: the 16,17[(cyclohexylmethylene)bis(oxy)]-11-hydroxy-21-(2-methyl-1-oxopropoxy)pregna-1,4-diene-3,20-dione [11beta, 16alpha (R,S)] obtained by the process described in WO 98/09982 has distinctly higher $X_{60}$ values. These are not in the range of $X_{60}$ values of particle sizes suitable for inhalation.

4: Preparation of the starting compounds of the formula I by acylation

A: 16,17-[(Cyclohexylmethylene)bis(oxy)]-11-hydroxy-21-(2-methyl-1-oxopropoxy)pregna-1,4-diene-3,20-dione [11beta, 16alpha(R,S)]

10 g of 16,17-[(cyclohexylmethylene)bis(oxy)]-11,21-dihydroxypregna-1,4-diene 3,20-dione [11beta, 16alpha (R,S)] and 6 g of potassium carbonate are suspended in 50 ml of acetone and, while stirring, 4.4 ml of isobutyric anhydride are added, and the mixture is heated under reflux for 2.5 h. After cooling to RT, 100 ml of water are slowly added to the suspension. The product is filtered off with suction, washed with water and dried. The enrichment of the R epimer takes place as described above.

Yield of crude product: 11.4 g (99.3% of theory) of 16,17-[(cyclohexylmethylene)bis(oxy)]-11-hydroxy-21-(2-methyl-1-oxopropoxy)pregna-1,4-diene-3,20-dione [11beta, 16alpha (R,S)]

Determination of the epimer ratios for compounds of the formula I

The epimer ratios are determined by HPLC.

HPLC conditions:
Column material: Hypersll C18, 5 μm, 125×4.6 mm
Detector wavelength: 242 nm
Sample concentration: 0.5-15 mg/ml
Volume loaded: 20 μl
Flow rate: 1 ml/min
Oven temperature 20° C.
Compound A: eluent water (45%)/ethanol (55%)

The invention claimed is:

1. A process for preparing a compound of the formula I

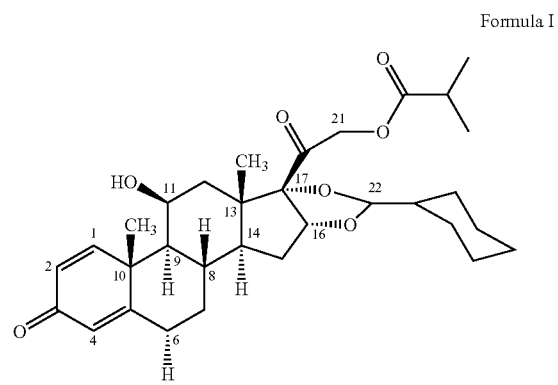

Formula I in crystalline form, with defined particle size, comprising the steps of
 a) preparing a solution of the compound of the formula I in a suitable water-miscible organic solvent;
 b) adding the solution obtained in a) to water and
 c) isolating a precipitate with a particle diameter for 50% of the total volume of all articles ($X_{50}$) of less than or equal to 3 μm of the compound of the formula I which is formed.

2. The process according to claim 1, characterized in that the suitable water-miscible organic solvent is an alcohol.

3. The process according to claim 2, characterized in that the alcohol is selected from the group consisting of methanol, ethanol, N-propanol, isopropanol and mixtures in any mixing ratio thereof.

4. The process according to claim 3, characterized in that the alcohol is ethanol.

5. The process according to claim 1, characterized in that the suitable water-miscible organic solvent is selected from the group consisting of acetone, tetrahydrofuran and dimethylformamide.

6. The process according to claim 1, characterized in that the temperature of the suitable water-miscible organic solvent is in the range from 15° C. to 10° C. below the boiling point of the solvent.

7. The process according to claim 6, characterized in that the temperature of the suitable water-miscible organic solvent corresponds to the room temperature at which the process is carried out.

8. The process according to claim 1, characterized in that the temperature of the water is from 10 to 50° C.

9. The process according to claim 7, characterized in that the temperature of the water corresponds to the room temperature at which the process is carried out.

10. The process according to claim 1, characterized in that, in step (a), the compound of the formula I is substantially in the form of the R epimer.

11. The process according to claim 10, characterized in that the proportion of R epimer in the compound of the formula I is more than 95%.

12. The process according to claim 10, characterized in that the compound of the formula I is ciclesonide.

13. The process according to claim 1, characterized in that the precipitate obtained in step c) is subsequently dried.

14. The process for preparing a compound of the formula I ng to claim 1 in crystalline form with defined particle size, comprising the steps of a) preparing a compound of the formula I by acylation of a compound of the formula II

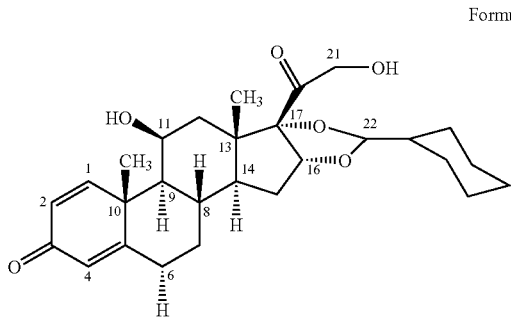

Formula II with a suitable acylating agent;
b) crystallizing the compound of the formula I obtained in a) by adding water to a solution of the compound in a suitable water-miscible organic solvent or heating a suspension of the compound of the formula I in a mixture of a suitable water-miscible organic solvent and water,
c) removing the resulting R epimer-enriched precipitate of the compound of the formula I from the water/solvent mixture;
d) if desired repeating step b);
e) preparing a solution of the compound obtained in c) in a suitable water-miscible organic solvent;
f) adding the solution obtained in e) to water and
g) isolating a precipitate with a particle diameter for 50% of the total volume of all particles ($X_{50}$) of less than or equal to 3 μm which has been formed of the compound of the formula I.

15. The process according to claim 1, where the particle size is characterized by an $X_{50}$ in the range from 1.8 to 2.0.

16. The process according to claim 14, where the organic solvents used in steps b) and e) are the same solvents.

* * * * *